(12) United States Patent
Tcherny et al.

(10) Patent No.: US 6,418,940 B1
(45) Date of Patent: Jul. 16, 2002

(54) INTERDENTAL DEVICE AND CONTAINER

(76) Inventors: Iosif Tcherny, 798 River Walk Dr., Wheeling, IL (US) 60090; Samuel N. Gomon, 1140 W. Northshore Ave., Chicago, IL (US) 60626

( * ) Notice: Subject to any disclaimer, the term of this patent is extended or adjusted under 35 U.S.C. 154(b) by 49 days.

(21) Appl. No.: 09/690,126

(22) Filed: Oct. 17, 2000

(51) Int. Cl.⁷ ............................................... A61C 15/00
(52) U.S. Cl. ......................................... 132/321; 433/80
(58) Field of Search ..................... 433/80, 81, 141, 433/216; 132/321, 328, 329

(56) References Cited

U.S. PATENT DOCUMENTS

| | | | | |
|---|---|---|---|---|
| 4,040,433 A | * | 8/1977 | Edison | 132/321 |
| 5,076,301 A | * | 12/1991 | Sulskis | 132/321 |
| 5,642,741 A | * | 7/1997 | Choi | 132/321 |
| 5,931,659 A | * | 8/1999 | Wu | 132/321 |
| 6,082,999 A | * | 7/2000 | Tcherny et al. | 132/321 |

* cited by examiner

Primary Examiner—Cary E. O'Connor

(57) ABSTRACT

A container and an interpick carried therein. The container is made up of an outer and in inner casing releasably held together. The casings are constricted as an a non-spill device, whereby none of the liquid therein will spill regardless of what position it assumes. An interpick is releasably carried in the container. Sealing elements with at least a predetermined yiedlability are interposed between the interpick and the inner casing and between the casings.

11 Claims, 5 Drawing Sheets

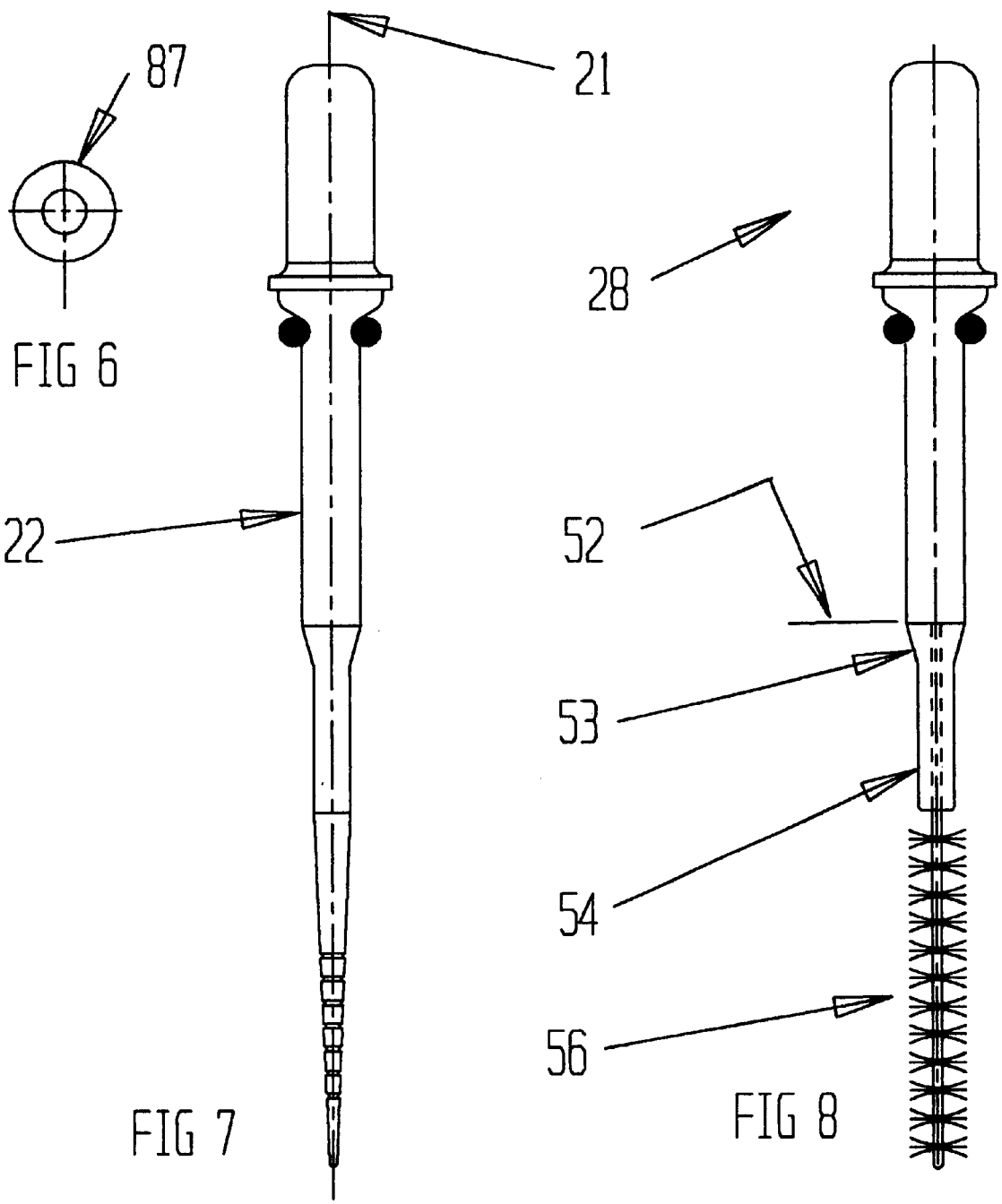

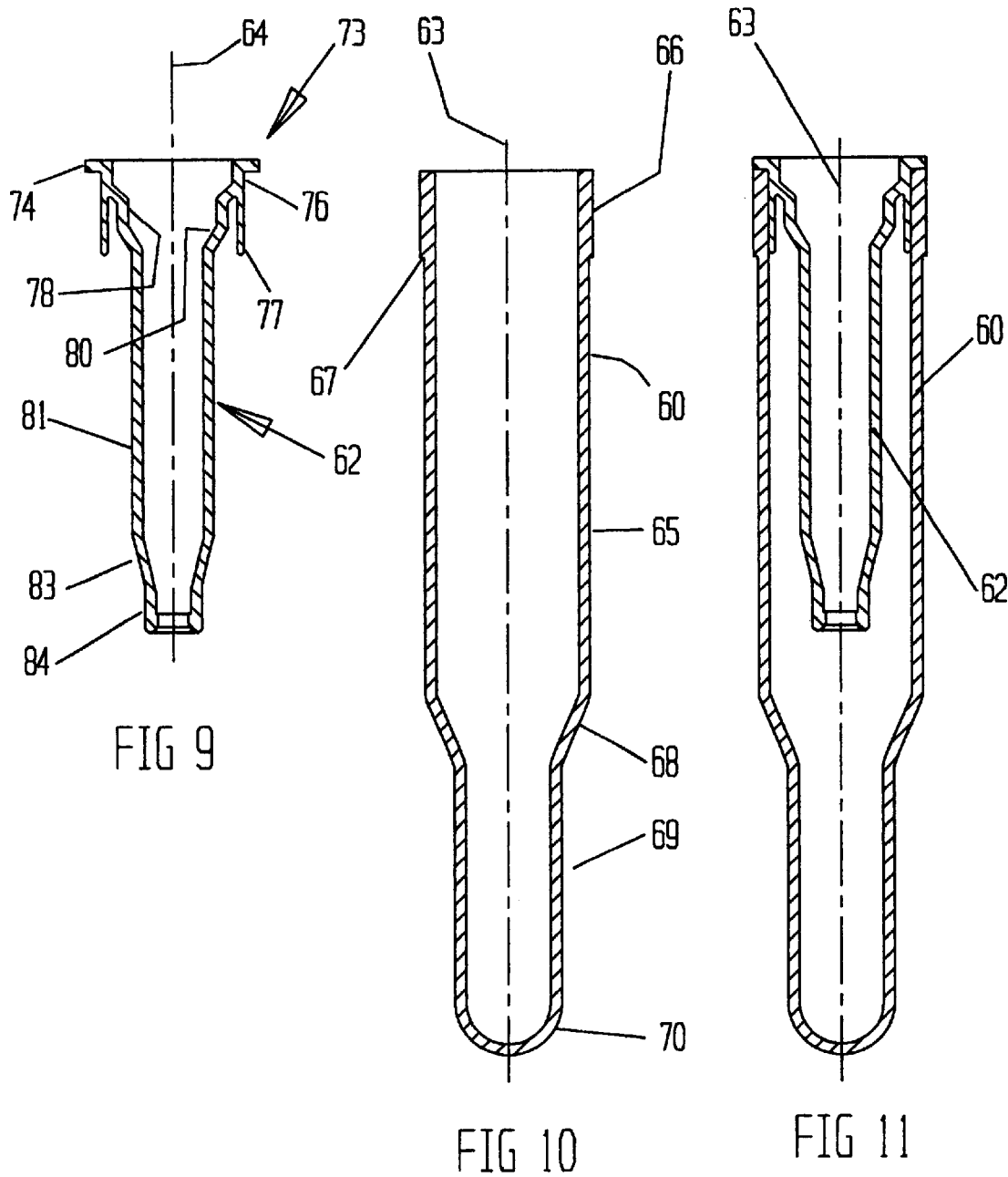

INTERDENTAL DEVICE AND CONTAINER

FIELD OF THE INVENTION

The invention resides in the field of dental devices that are small and easy to carry, such as in luggage, or even on the person. The device contains an interdental pick and in certain cases a brush, which is carried in a container, the container also including a liquid therein, such as a dental rinse, dental jell, paste for medication.

Attention is directed to our earlier U.S. Pat. No. 6,082,999, dated Jul. 4, 2000.

SUMMARY OF THE INVENTION

The device of the invention is in general similar to that of our prior patent referred to.

An important feature of the invention is the provision of such a device, which has a novel construction for eliminating leakage in the container in which the pick is carried.

The container is made up of two parts, fitted together and held together by friction. The pick can be inserted into and withdrawn from the container, when the container is assembled, and held in the container by friction between the interengaging elements.

A broad object therefore is to provide such a container having novel features for preventing leakage of the liquid in the container at those point of interengagement and separation of the parts of the container, and between the container and the inserted pick.

BRIEF DESCRIPTIONS OF THE INDIVIDUAL FIGURES OF THE DRAWINGS

FIG. 6 is a face view of an O-ring sealing element.

FIG. 7 is a view of the pick shown in FIG. 1 and oriented similarly thereto.

FIG. 8 is a view of the pick of FIG. 2 and oriented similarly thereto.

FIG. 9 is a longitudinal sectional view of the inner casing of the container.

FIG. 10 is a longitudinal sectional view of the outer casing of the container.

FIG. 11 is a view showing the casing of FIGS. 9 and 10 assembled.

DETAILED DESCRIPTION OF THE ACCOMPANYING DRAWINGS

Figure 1:
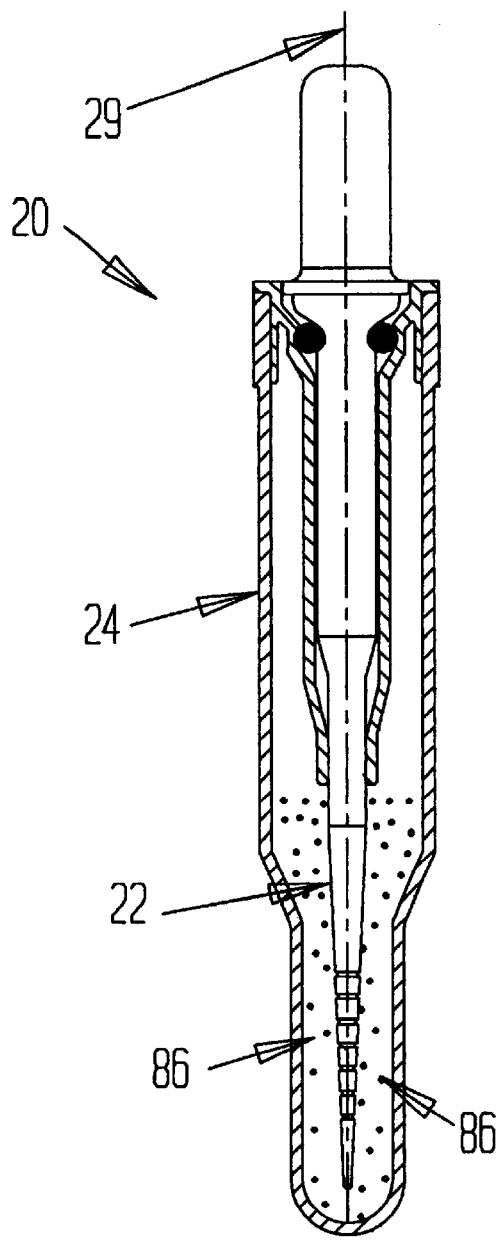
FIG. 1 is a longitudinal sectional view through the assembled device.
Figure 2:
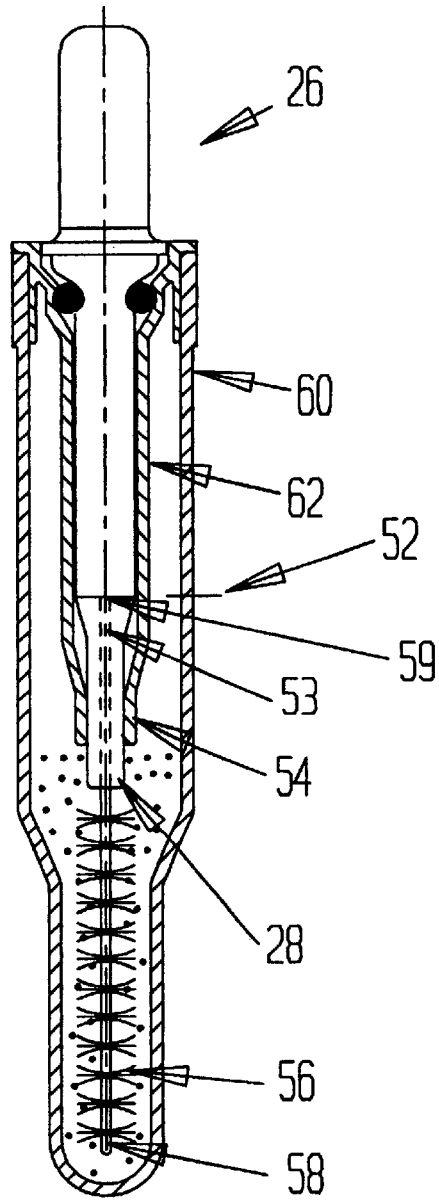
FIG. 2 is a view similar to FIG. 1 but with a modified form of pick, the containers in both cases being identical.
Figure 3:
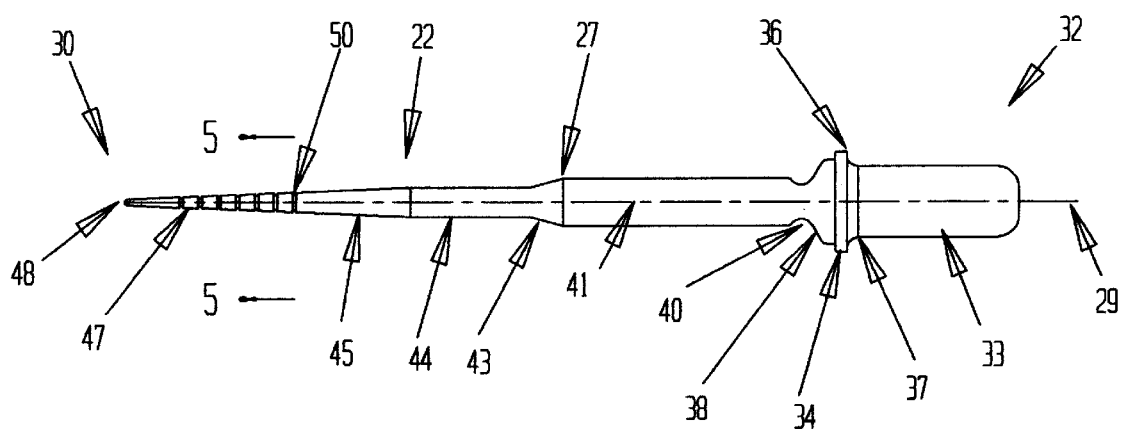
FIG. 3 is a side face view of the pick shown in FIG. 1.

Attention is directed first to FIGS. 1 and 2, both of which show the entire device, but having relatively modified forms of pick or interpick. Referring first to FIG. 1, the entire device is shown at 20, which includes a pick 22 (see also FIG. 7), and the entire container (see also FIG. 11).

Referring to FIG. 2, this figure includes an entire device 26, having a pick or interpick 28 (see also FIG. 8) which is different from the pick 22 of FIG. 1. The details of both of these picks are given hereinbelow.

The various parts and elements, except a resilient seal, and a twisted wire, are preferably made of molded or expanded plastic although the invention is not limited to such materials.

Reference is first made to the pick 22, as shown in FIGS. 1, 2–7. The pick 22 is an integral one-piece item. It includes a main shank 27, extending nearly the length of the pick. This shank may also be referred to as a stem, or central core. It has a longitudinal central axis 29 and what is referred to for convenience as a lower or inner end 30 and an outer or upper end 32. The pick at its outer end has a handle 33, and inwardly of the handle, a cap unit 34. This unit serves as a closure to the inner container as will be described in detail hereinbelow, and includes a relatively large cylindrical flange 36 of short axial dimension, and smaller elements 37, 38 on the outer and inner sides of the flange, respectively. Inwardly of the element 38 is a circumferential groove 40.

The shank 27 includes an outer cylindrical segment 41 of largest diameter. The next is a short conical segment 43 which leads into another cylindrical segment 44 of smaller diameter than the segment 41. Inwardly of the segment 44 is a conical segment 45, inwardly of which is another conical segment 47, of smaller diameter than the segment 45 and may be a continuation of the latter. Forwardly of the segment 47 is a point 48 of small diametrical or transverse dimensions.

Figures 4, 5:
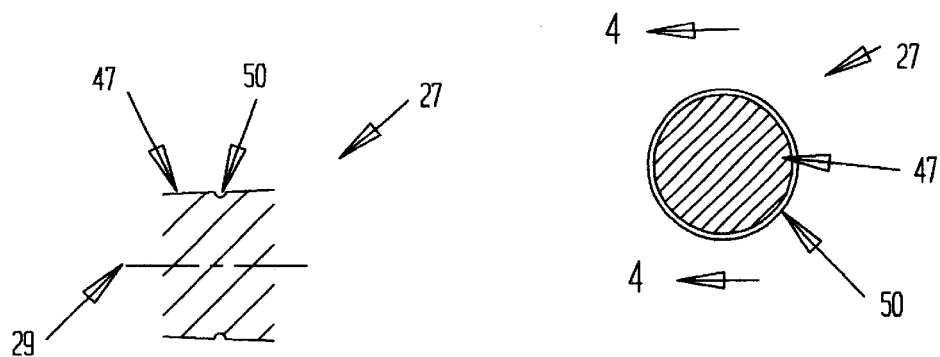
FIG. 4 is a view taken at line 4—4 of FIG. 5.
FIG. 5 is a sectional view taken at line 5—5 of FIG. 3.

The segment 47 is provided with a series of circumferential or peripheral grooves 50 (see also FIGS. 4 and 5).

The foregoing consists of the description of the complete pick 22, and reference is now made to the pick 28 of FIGS. 2 and 8. In the pick 28, the upper part above the line 52 is identical with the pick 22. Proceeding inwardly from the line 52 is a short conical segment 53 which leads into a cylindrical segment 54 of smaller diameter. The inner segment 54 and the remainder outwardly thereof constitute a rigid shank or stem.

The pick 26 is in the form of a brush 56 which includes a central twisted wire core 58, the upper end of which, 59, is imbedded in the segment 54. The twisted wire may be of metal and the bristles are preferably plastic and quite flexible transversely, but having a substantial degree of stiffness in longitudinal direction for producing the desired brushing effect.

Reference is now made to the container 24 as shown particularly in FIGS. 1, 2, 9–11.

The entire container includes an outer casing 60, and an inner casing 62, having longitudinally central axes 63, 64. These two casings are assembled as shown in FIG. 11, in the completed structure of the device. The outer casing 60 includes a main outer cylindrical portion 65 having at its extreme upper or outer end a flange 66, the latter forming an outer circumferential support surface 67 utilized in the steps of fabrication of the casing. Next inwardly, is a conical segment 68 of relatively short length which merges into another cylindrical segment 69, the latter being closed by a spherical segment 70.

The inner casing 62, as noted above, is inserted in the outer casing 60. The inner casing 62 has a structural unit 73 for forming a sealing effect, including a radially outwardly extending flange 74. At the radially inner edge of the flange is a segment 76 of relatively greater radial thickness, which includes a longitudinally inwardly extending cylindrical skirt 77 of radially less thickness than the segment 76, for providing a sealing effect as referred to again hereinbelow. Inwardly of the skirt 76, is a cylindrical segment 77 spaced from the skirt and forming an extension of the segment 76. This segment 77 is relatively short, and leads into a conical segment 80 which in turn leads into a relatively long cylindrical segment 81. The segment 81 merges into another conical segment 83, and the latter merges into a cylindrical segment 84. The overall effect is reduction of diameter throughout the length of the inner casing from the outer end to the inner end, and the inner end is open, as contrasted with the inner end of the outer casing 60.

The inner casing 62 (FIG. 9) is inserted into the upper open end of the outer casing 60 (FIG. 10) to the position shown in FIG. 11. In this position the flange 74 fits down against the upper edge surface of the outer casing, and the skirt 77 extends its full length down into the outer casing. As noted, the lower portion of the skirt is relatively flexible, and it is thinner than the upper edge of the outer casing, and the skirt because of its flexibility, is easily inserted into the outer casing, and the skirt readily adapts to a full surface engagement with the inner surface of the outer casing. This flexibility of the skirt provides greater sealing effect, and prevents leakage of liquid between itself and the outer casing, which is one of the main features of the invention, namely, the leakage of liquid therethrough. It will be noted (FIG. 11) that the areas of engagement form an inside corner, of 90 degrees. This change in direction forms a factor in the prevention of leakage.

The assembly of the casings (FIG. 11) holds the pick 22, the latter being inserted through the upper open end of the assembled container to the position shown in FIG. 1. The liquid is shown at 86 (FIG. 1) and the inner end of the pick extends down into the liquid, when in upright position, and performs its function of sterilizing and cleaning the pick.

Another important feature is the prevention of leakage of the liquid between the pick and the inner casing, which is best shown in FIG. 1. A resilient O-ring 87 is fitted in the groove 40 (FIG. 3) and frictionally held therein. Upon insertion of the pick into the assembled container, the O-ring engages the inner cylindrical surface 78. The normal outer diameter of the ring is greater than the diameter of the surface 78, and functions to prevent leakage at that point. Although the ring normally frictionally holds the pick in place, it will readily yield to enable release of the pick, in response to the user grasping the handle and withdrawing the pick. Referring to FIG. 1, it will be noted that the inner casing, along with the pick, is held in place in the outer casing by the engagement at the upper end of the two casings of the container. The lower end of the inner casing is free, relative to the outer casing.

In use of the device, the user picks up the entire device, and holds it in one hand and by grasping the handle 33 withdraws the pick for use. In the case of the pick 22 (FIG. 1) the inner-most point may be used as a toothpick, and the inner segment may be extended into space between the teeth. This includes the segment 47 which contains the grooves 50, of varying sizes, for removing relatively large particles of food from between the teeth and delivery of dental liquids, jells, paste or medication.

The use of the pick 26 (FIG. 8) is substantially the same as that of the pick 22. It is mounted in the inner casing in the same manner, and the bristles 56 extend down beyond the lower end of the inner casing, into the liquid. The two picks are essentially the same, from the standpoint of inserting them into the container and withdrawing them, but the two picks are different in the detailed use, one having a solid point 47, and the other having bristles 56.

Figure 12:
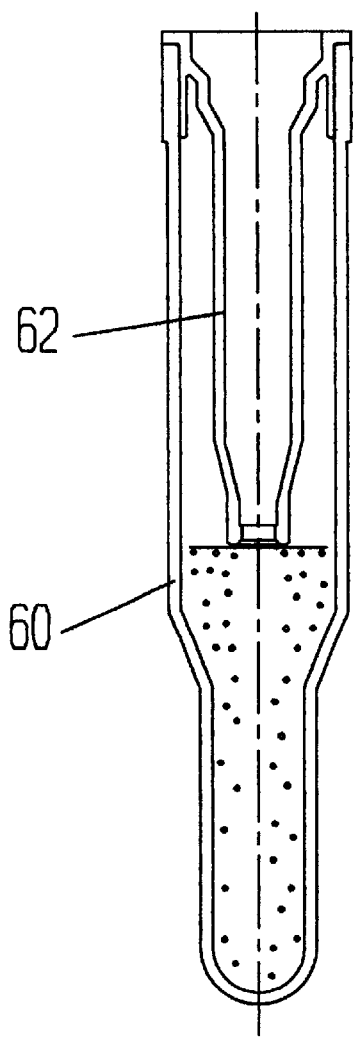
FIG. 12 is a view similar to FIG. 11 with liquid shown in the container.
Figure 13:
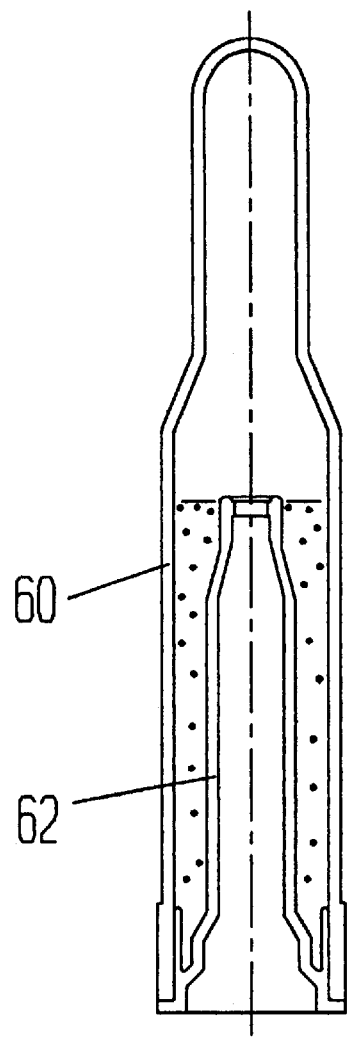
FIG. 13 is a view inverted relative to FIG. 12 showing the liquid therein, consequently showing the liquid surrounding the inner casing.
Figure 14:
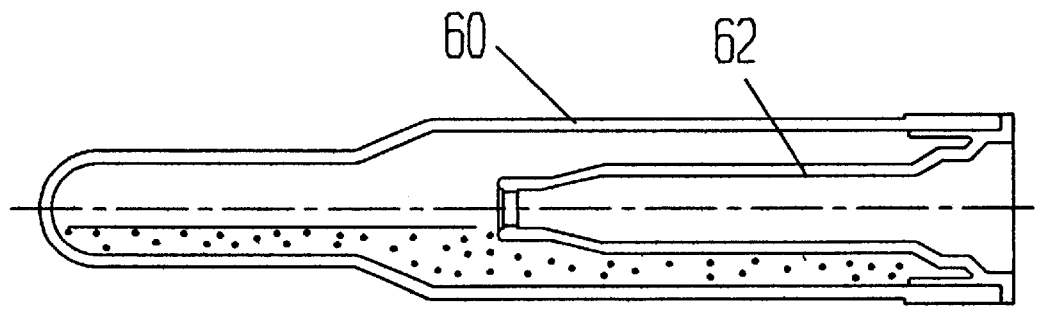
FIG. 14 is a view of the container of FIGS. 12 and 13, lying horizontally on its side.

FIGS. 12–14 show the relationship of the sizes of the inner and outer casings, and how the liquid is retained in the outer casing. Even if the pick is removed from the outer casing, and the outer casing is set on a surface in any position, the liquid will not flow out. The inner casing is of such length that its inner end is so positioned that the quantity of liquid that can be held in the interior space, between the casings, will not flow out in any position of the device. Preferably the inner end of the inner casing is at the volumetric center of the interior space, in which position it enables a maximum amount of liquid without overflow of liquid to the exterior. In such proportions of the casings, that maximum amount of liquid is as represented in FIG. 13. The novel sealing features of the invention effectively overcome imperfections that may occur in manufacturing steps. Other obstacles that are overcome include those that are caused by capillary action and changes in volume produced by changes in temperature.

What is claimed is:

1. A dental device comprising,
   an interpick,
   a container,
   the interpick and the container each including an outer end and an inner end,
   the interpick including a pick element at its inner end,
   the container being adapted to hold a quantity of liquid, jell, paste or medication,
   the interpick being adapted to be fitted in the container, and when therein, to extend into the liquid,
   the container including an outer casing and an inner casing, and
   the device including a resilient sealing means operably positioned between the interpick and the inner casing.

2. A dental device according to claim 1, wherein,
   the resilient sealing means is constituted by an O-ring encircling the interpick.

3. A dental device according to claim 2, wherein,
   the interpick includes at its inner end a segment of solid uniform material having a point at its extreme inner end and circumferential grooves outwardly of the point.

4. A dental device according to claim 3, wherein,
   the interpick is of continuous uniform material throughout its extent.

5. A dental device according to claim 1, wherein,
   the interpick includes a longitudinally outer portion forming a rigid stem, and
   longitudinally inner portion formed by a brush which includes a series of bristles.

6. A dental device according to claim 5, wherein,
   the brush includes a central core formed by twisted wires in which the bristles are held,
   the interpick includes a longitudinally outer portion forming a rigid stem, and
   the core of the brush has an outer end embedded in the rigid stem.

7. A dental device comprising,
   a container,
   an interpick,
   the container being made up of an outer casing and an inner casing, the interpick and the casings each having an outer end and an inner end the device correspondingly having an outer end and an inner end, the outer casing being of tubular form with its outer end open and being otherwise closed, the inner casing being of tubular form, open at both ends, and shorter than the outer casing, the inner casing being insertable into the outer casing, to an operable position where the outer ends of the two casings are closely adjacent, the inner casing including a cylindrical skirt having an outer end integral with the remainder of the inner casing, and an inner end free of the remainder of the inner casing, the inner end of the skirt being thinner than the outer end thereof, and thereby being radially spaced outwardly from the remainder of the inner casing.

8. A dental device according to claim 7 wherein, the inner casing includes, in its sealing unit, a radially outwardly extending flange fitted on and engaging the outer end surface of the outer casing, whereby the sealing unit forms an outer peripheral recess receiving the outer end of the outer surface.

9. A dental device according to claim 8 wherein, the outer casing includes a radially thickened portion at its outer end, extending axially substantially the length of the skirt, and the skirt engages the outer casing throughout this length.

10. A dental device accordance with claim 7 wherein, the interpick includes a closure unit adjacent its outer end which includes a plate-like circular closure element fitted in the annular flange on the outer casing, and the device includes a resilient sealing element between the interpick and the inner casing.

11. A dental device comprising, a container, an interpick, the container including an outer casing and an inner casing, the outer casing having an opening and being otherwise closed, the inner casing being tubular and open at both ends, the casings being capable of being fitted together with the inner end of the inner casing extending into the outer casing and the outer open of the inner casing being adjacent each other, a tubular element on one of the casings sealing the casings against leakage therebetween, the container being capable of containing a predetermined quantity of liquid between the casings, the casings being relatively dimensioned so as to prevent leakage from the container in any position of the container, the interpick being extendable through the inner casing and thereby fitted in the container, and the container including sealing means of at least a predetermined resiliency between the interpick and the inner casing, and between the casings respectively.

\* \* \* \* \*